(12) United States Patent
Choksi et al.

(10) Patent No.: US 9,925,229 B1
(45) Date of Patent: Mar. 27, 2018

(54) ANTI-AGING COMPOSITION METHOD

(71) Applicant: PALEO LIFE, LLC, Sunrise, FL (US)

(72) Inventors: Tejas Choksi, Sunrise, FL (US); Ludwig Johnson, Sunrise, FL (US)

(*) Notice: Subject to any disclaimer, the term of this patent is extended or adjusted under 35 U.S.C. 154(b) by 5 days.

(21) Appl. No.: 14/884,341

(22) Filed: Oct. 15, 2015

(51) Int. Cl.
| | |
|---|---|
| *A61K 36/9066* | (2006.01) |
| *A61K 36/53* | (2006.01) |
| *A61K 36/87* | (2006.01) |
| *A61K 36/63* | (2006.01) |
| *A61K 9/127* | (2006.01) |
| *A61K 47/24* | (2006.01) |
| *A61K 9/48* | (2006.01) |
| *A61K 9/14* | (2006.01) |
| *A61K 47/12* | (2006.01) |
| *A61K 47/36* | (2006.01) |
| *A61K 47/02* | (2006.01) |
| *A61K 47/46* | (2006.01) |

(52) U.S. Cl.
CPC .......... *A61K 36/9066* (2013.01); *A61K 9/127* (2013.01); *A61K 9/14* (2013.01); *A61K 9/4816* (2013.01); *A61K 36/53* (2013.01); *A61K 36/63* (2013.01); *A61K 36/87* (2013.01); *A61K 47/02* (2013.01); *A61K 47/12* (2013.01); *A61K 47/24* (2013.01); *A61K 47/36* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 5,519,159 A * | 5/1996 | Narabe | C07F 9/103 558/146 |
| 8,741,357 B2 | 3/2014 | Lintner et al. | |
| 2007/0166253 A1* | 7/2007 | Kostick | A61K 8/97 424/63 |
| 2007/0196318 A1* | 8/2007 | Marini | A61K 8/97 424/74 |
| 2009/0017147 A1* | 1/2009 | Lintner | A61K 8/975 424/780 |
| 2012/0156272 A1* | 6/2012 | Rebmann | A61K 36/23 424/401 |
| 2013/0217768 A1* | 8/2013 | Nahas | A23L 1/3002 514/533 |

FOREIGN PATENT DOCUMENTS

WO  WO-2013-093881  *  6/2013

OTHER PUBLICATIONS

Yu J-N, Enhancement of oral bioavailability of the poorly water-soluble drug silybin by sodium cholate/phospholipid-mixed micelles, Acta Pharmacologica Sinica, 2010, 31, 759-764.*

* cited by examiner

*Primary Examiner* — Celeste A Roney
(74) *Attorney, Agent, or Firm* — Sanchelima & Associates, P.A.; Christian Sanchelima, Esq.; Jesus Sanchelima, Esq.

(57) ABSTRACT

An anti-aging composition, having anti-oxidant and anti-inflammatory properties, comprised of an effective amount of Turmeric Root Extract, Olive Leaf Extract, Grape Seed Extract, and Rosemary Leaf Extract to regulate and slow the signs of skin aging and tired looking skin. The composition also includes characteristics that may help to prevent cancer. The composition implements liposomal technology, using phosphatidylcholine, to surround the active ingredients with lipid molecules, thereby increasing the bioavailability of the present composition.

5 Claims, No Drawings

ANTI-AGING COMPOSITION METHOD

BACKGROUND OF THE INVENTION

1. Field of the Invention

The present invention relates to a composition and, more particularly, to an anti-aging composition using liposomal technology for more effective absorption by the body.

2. Description of the Related Art

Several formulations for anti-aging compositions have been created in the past. None of them, however, include the unique and effective blend of Curcumin, Olive Leaf Extract, Grape Seed Extract, Oligomeric Procyanidinds, and Rosemary Leaf Extract in the novel proportions found in the present composition.

Applicant believes that a related reference corresponds to U.S. Pat. No. 8,741,357 issued to Sederma SAS for a cosmetic or derma pharmaceutical composition comprising a *euglena* extract. However, it differs from the present invention because the Sederma reference does not disclose or motivate one of ordinary skill in the art to combine the in ingredients subject of the present invention by using ingredients subject of the present invention in the proportions disclosed herein.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a composition with anti-aging qualities derived from anti-oxidants and anti-inflammatory characteristics of the ingredients in the present composition.

It is another object of this invention to provide a composition with immune boosting properties to assist warding off infections, cancer and other illnesses.

It is still another object of the present invention to provide a composition that uses liposomal technology to create a composition with a higher bioavailability to magnify its health benefits.

It is another object of this invention to provide a composition that helps lower diabetes.

It is yet another object of this invention to provide such a composition that is inexpensive to implement and maintain while retaining its effectiveness.

Further objects of the invention will be brought out in the following part of the specification, wherein detailed description is for the purpose of fully disclosing the invention without placing limitations thereon.

DETAILED DESCRIPTION OF THE EMBODIMENTS OF THE INVENTION

Referring now to the drawings, where the present composition includes a blend of ingredients in a powder or capsule for compromising of the following active ingredients: Turmeric Root Extract; Olive Leaf Extract; Grape Seed Extract Phosphatidylcholine; and Rosemary Leaf Extract. The present invention further includes the following ingredients: Maltodextrin, Malic Acid, Natural Pineapple Flavor, *Stevia* Leaf Extract, and Silicon Dioxide.

The present invention uses liposomal technology wherein the Phosphatidylcholine, a lipid in powdered form, is put in contact with water to create micelles having a hydrophilic head and a hydrophobic tail. These components of the micelles have a spherical arrangement that surround the active ingredients or molecules of the present composition. Since the cell walls of an organism are made of lipids, the body readily absorbs the active ingredients surrounded by the lipids increasing the bioavailability of the present composition.

In a preferred embodiment, the present invention in a three (3) gram serving includes the following effective proportions: Turmeric Root Extract (with 90-99% curcumin concentration) 100 mg-500 mg by weight; Olive Leaf Extract (having concentration of oleuropein of 10%) 100 mg-500 mg by weight; Grape Seed Extract (having 95% oligomeric procyanidins) 25 mg-250 mg by weight; Rosemary Leaf Extract (having 1.5%-6% rosamarinic acids) 25 mg-100 mg by weight; and Phosphatidylcholine (with a purity between 20-40%) 500 mg-1000 mg by weight.

Turmeric (a root) when grounded into a powder only has about 2-3% of the standardized curcumin alkaloid. In the present composition, the curcumin is many times more concentrated having a curcumin concentration of 95%. The inactive ingredients include maltodextrin used as a filler and taste enhancer. Malic acid is also used as a filler and to reduce the pH of the present composition, thereby giving it a citric taste.

The olive leaf extract having 10% oleuropein can be represented as having a 10:1 ratio. For example, through an herbal extraction process, ten kilograms of olive leaf powder can be used to make one kilogram of concentrated powder that has 10% oleuropein extract.

Present composition's active ingredients can be formulated using the following effective ranges in percentages by weight:

Turmeric Root Extract 3%-17% by weight;
Olive Leaf Extract 3%-17% by weight;
Grape Seed Extract 0.8%-9% by weight;
Rosemary Leaf Extract 0.8%-3% by weight; and
Phosphatidylcholine 17%-33% by weight.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A composition subject in capsule form having improved bioavailability containing micelles consisting of:
   Turmeric Root Extract between 3%-17% by weight;
   Olive Leaf Extract between 3%-17% by weight;
   Grape Seed Extract between 0.8%-9% by weight;
   Rosemary Leaf Extract between 0.8%-3% by weight;
   Phosphatidylcholine between 17%-33% by weight wherein said phosphatidylcholine includes between 20%-40% purity.

2. The composition subject of claim 1 wherein said rosemary leaf extract includes between 1.5%-6% of rosmarinic acid concentration.

3. The composition subject of claim 1 wherein said turmeric root extract includes between 90-99% of curcumin concentration.

4. The composition subject of claim 1 wherein said olive leaf extract includes 10% of olueropein concentration.

5. A composition subject of claim 1 including:
   Turmeric Root Extract 5% by weight;

Olive Leaf Extract 3.33% by weight;
Grape Seed Extract 0.833% by weight;
Rosemary Leaf Extract 0.833% by weight; and
Phosphatidylcholine 17% by weight.

* * * * *